US012570589B2

(12) United States Patent
Rohleder et al.

(10) Patent No.: US 12,570,589 B2
(45) Date of Patent: Mar. 10, 2026

(54) MEMBRANE PROCESS FOR BUTADIENE EXTRACTION SOLVENT PURIFICATION

(71) Applicant: EXXONMOBIL TECHNOLOGY AND ENGINEERING COMPANY, Annandale, NJ (US)

(72) Inventors: Andrew J. Rohleder, Baton Rouge, LA (US); Bhupender S. Minhas, Bridgewater, NJ (US); David B. Spry, Prairieville, LA (US); Michelle E. Dose, Martinsville, NJ (US); Neel Rangnekar, Whitehouse Station, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 53 days.

(21) Appl. No.: 18/366,131

(22) Filed: Aug. 7, 2023

(65) Prior Publication Data

US 2024/0051902 A1     Feb. 15, 2024

Related U.S. Application Data

(60) Provisional application No. 63/370,806, filed on Aug. 9, 2022.

(51) Int. Cl.
| | |
|---|---|
| *C07C 7/144* | (2006.01) |
| *B01D 71/02* | (2006.01) |
| *C07C 7/00* | (2006.01) |
| *C07C 7/10* | (2006.01) |

(52) U.S. Cl.
CPC .............. *C07C 7/144* (2013.01); *B01D 71/02* (2013.01); *C07C 7/005* (2013.01); *C07C 7/10* (2013.01)

(58) Field of Classification Search
CPC ........... C07C 7/144; C07C 7/005; C07C 7/10; B01D 71/02; B01D 2311/25
See application file for complete search history.

(56) References Cited

FOREIGN PATENT DOCUMENTS

WO        WO-9813439 A1 *  4/1998   ............... C10C 1/00

* cited by examiner

*Primary Examiner* — Thuan D Dang
(74) *Attorney, Agent, or Firm* — WOMBLE BOND DICKINSON (US) LLP; Kevin J. Davis

(57)                  ABSTRACT

The present disclosure is directed to 1,3-butadiene extraction and steam cracking recovery systems, more particularly, to systems and methods for removing tar from the solvent loop of such systems using a membrane.

17 Claims, 6 Drawing Sheets

MEMBRANE PROCESS FOR BUTADIENE EXTRACTION SOLVENT PURIFICATION

FIELD OF THE INVENTION

The present disclosure is directed to 1,3-butadiene extraction and steam cracking recovery systems, more particularly, to systems and methods for removing tar from the solvent loop of such systems using a membrane.

BACKGROUND

The 1,3-butadiene (BD) extraction process is typically found coupled with steam cracking recovery trains as the disposition for bulk (or crude) C4 streams. BD (C4H6) separates with this stream; the molecule is a high-value coproduct of steam cracking at product grade (99.5 wt %) for use in the manufacture of synthetic rubber.

Extractive distillation is utilized to selectively remove BD from the bulk C4 stream due to the narrow boiling point range of the various molecules, which make separation by traditional distillation impractical. Multiple BD extraction technologies are licensed for implementation with a key differentiator being the solvent used. For example, Nippon Zeon technology which utilizes dimethylformamide as the extractive solvent. Other technologies include an acetonitrile (ACN) process from Shell as well as an N-methylpyrrolidine (NMP) process from Lummus/BASF. DMF carries a significant cost and availability advantage over ACN and NMP, however, the technology is vulnerable to rate-limiting, solvent-induced fouling.

The interaction of DMF with BD will lead to the formation of tar. Tar formation is a constant mechanism within the unit as fresh hydrocarbon feed is met with DMF; the rate of tar formation within the unit is quite small as a percentage of the feed rate, but the tar accumulates over time in the solvent loop. While the tar is considered soluble in DMF under healthy circulating solvent conditions, it will deposit on process equipment over the course of the unit's run length. Unhealthy circulating solvent conditions prompted by an inability to remove tar, poor operating envelope management, or any variety of disadvantaged solvent conditions can lead to accelerated unit fouling due to tar insolubility.

Tar deposition can impact the unit in a variety of ways, as summarized by Table 1 below.

TABLE 1

| Equipment | Mechanism of Deposition | Consequence |
|---|---|---|
| Distillation Column | Plating out on tray active area | Early-onset tower flooding |
|  | Restricting downcomer outlet | Throughput limitations |
| Heat Exchanger | Restricting/plugging of tube side | Elevated steam usage due to reboiler fouling |
|  | Plating out on shell side | Throughput limitations Elevated maintenance costs due to frequent exchanger cleanings |
| Instrumentation | Restricting/plugging instrument taps | Poor instrumentation reliability Elevated maintenance costs due to frequent break-in work |

The most conventional mechanism for removing tar is an in-line strainer. Strainer swaps occur on a frequent (<1 month) basis as DP across the equipment increases. Due to the typical solubility of tar in DMF, the pump strainers can only remove insoluble tar from the circulating solvent while the majority of soluble tar continues with the solvent.

Similarly, DMF vaporization is a common mechanism for removing soluble tar from the unit. In order to maintain an adequate rate of tar removal, a "tar purge" is controllably removed from the greater circulating solvent loop and fed to a kettle reboiler colloquially called a tar kettle. The tar kettle, operating under vacuum to lower the boiling point of the DMF, flashes off a portion of the DMF feeding it while retaining an approximately 70/30 mixture by weight of tar to DMF. Some DMF is retained in the tar to ensure the viscosity is low enough to freely flow and can be pumped out of the system. The tar kettle fills to a full level with the tar/DMF mixture, at which point the operations team swaps the tar purge to the spare tar kettle and empties the full kettle to the tar line using nitrogen pressure. This fill and swap procedure is typically executed on a daily to weekly basis.

Historically, the tar kettle system has ran into a variety of constraints that limit the unit's ability to maintain a consistent circulating tar content of 1 wt %. For example, some DMF in the tar kettle product is necessary to maintain tar viscosity. While the intention is to target a 70/30 tar to DMF mixture, the kettles have been shown to struggle historically to maintain this 30 wt % DMF target as tar purge rates are elevated. Due to this inefficiency, greater tar purge rates proportionately greater DMF losses. Similarly, tar kettles, by nature of their service, foul as the deposited tar covers the outside of the tube bundle. The kettle's heat transfer coefficient decreases which leads to incrementally more steam required to maintain the vapor outlet temperature operating target. Under fouled conditions, the kettle is operated at a maximum heat input limit. At this point, the kettle cannot maintain the targeted 70/30 tar to DMF mixture and begins giving away excess DMF. The tar purge rate cannot be raised without elevating the rate of DMF giveaway.

All of the conventional methods result in a monetary loss from DMF loss as well as an efficiency loss due to the need to shut down units for tar removal. As such, there remains a need for improved processes for removal of tar accumulations within the circulating solvent while minimizing or eliminating the need for unit shut down and/or loss of solvent.

BRIEF SUMMARY OF THE INVENTION

Membrane, a low energy separation technology, can be used to separate hydrocarbon molecules, based on solubility/diffusivity mechanism for polymeric membranes or pore flow in ceramic membranes. Polar molecules permeate through the membrane preferentially over non-polar molecules in polymeric membrane under solution/diffusion mechanism. Ceramic membrane largely works on size exclusion. FIG. below illustrates the concept of membrane separation of tar from extraction solvent dimethylformamide (DMF). Feed is pressurized to the membrane which allows polar molecule DMF to go through the membrane under solution/diffusion mechanism. Driving force for the permeating molecules, pressure differential, is provided by keeping the permeate side at lower pressure than the feed pressure.

In one aspect, the disclosure provides a method for removing tar from the solvent stream of an extraction unit, comprising:

feeding a solvent stream containing tar into a solvent recycle loop comprising a membrane unit;

preferentially permeating solvent in the solvent stream via the membrane unit to separate a tar rich stream from a membrane unit product stream; and feeding the membrane unit product stream into the solvent recycle loop for recirculation within the solvent recycle loop.

In certain embodiments of the method of the disclosure, the solvent recycle loop further comprises a reclaimer. In particular such embodiments, the method of the disclosure further comprises a step of processing the tar rich stream in the reclaimer, wherein the processing deposits tar into a tar kettle for removal from the extraction unit and produces a reclaimer treated stream. In some embodiment of the method of the disclosure, the reclaimer treated stream is fed into the solvent recycle loop for recirculation within the solvent recycle loop.

In certain embodiments of the method of the disclosure, the solvent stock stream comprises dimethylformamide.

In other embodiments of the method of the disclosure, preferentially permeating the solvent from the solvent stream via the membrane unit further comprises feeding the solvent stream into the membrane unit at a constant pressure between 50 to 3000 psig.

In still other embodiments of the method of the disclosure, the membrane unit comprises a one-stage membrane system. In yet other embodiments of the method of the disclosure, the membrane unit comprises a multi-stage membrane system. In certain embodiments of the method of the disclosure the membrane unit presents a solvent permeance of 120 $gm/m^2/hr/psi$.

In yet other embodiments of the method of the disclosure, the membrane unit is positioned upstream from the reclaimer. In some embodiments of the method of the disclosure, the solvent recycle loop comprises one or more additional membrane units. In certain embodiments of the method of the disclosure, one or more additional membrane units are positioned between the membrane unit and the reclaimer. In still other embodiments of the method of the disclosure, the one or more additional membrane units are positioned downstream from the reclaimer.

In another aspect, the invention provides a 1-3 butadiene extraction system, comprising:
a. an extraction unit configured to extract 1-3 butadiene from a solvent;
b. a solvent recycling loop configured to remove solvent containing tar or other heavy impurities from the extraction unit and to return cleaned solvent into the extraction unit;
c. one or more membrane units configured to receive solvent containing tar or other heavy impurities and to separate membrane-cleaned solvent from tar-rich solvent;
d. a reclaimer configured to receive tar-rich solvent and to extract tar or other heavy impurities from reclaimer-cleaned solvent; and
e. one or more recycling inlet ports configured to return the membrane-cleaned solvent and the reclaimer-cleaned solvent to the solvent recycling loop.

In certain embodiments of the system of the disclosure the solvent containing tar or other heavy impurities is fed into the membrane unit at a constant pressure between 50 to 3000 psig.

In other embodiments of the system pf the disclosure, the membrane unit comprises a one-stage membrane system or a multi-stage membrane system.

4

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various steps, features and combinations of steps/features described below and illustrated in the figures can be arranged and organized differently to result in embodiments which are still within the spirit and scope of the present disclosure. To assist those of ordinary skill in the art in making and using the disclosed systems, assemblies and methods, reference is made to the appended figures, wherein.

DETAILED DESCRIPTION OF THE INVENTION

Figure 1:
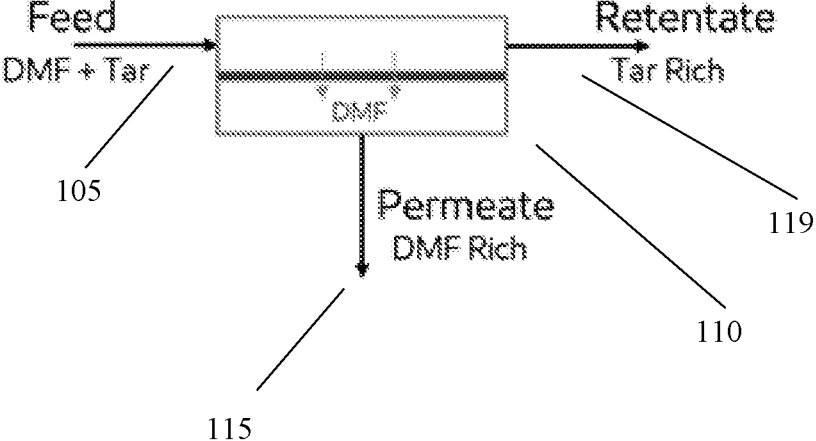
FIG. 1 is diagram depicting the general flow streams in a membrane DMF purification process

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

All numerical values within the detailed description and the claims herein are modified by "about" or "approximately" the indicated value, and take into account experimental error and variations that would be expected by a person having ordinary skill in the art.

The following terms are used to describe the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

It is also to be understood that the mention of one or more method steps does not preclude the presence of additional method steps or intervening method steps between those steps expressly identified, nor is the disclosure limited by the order in which the method steps are expressly identified. Similarly, it is also to be understood that the mention of one or more components in a system does not preclude the presence of additional components or intervening components between those components expressly identified, nor is the disclosure limited by the order in which the components are expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

Disclosed herein, therefore, are systems and methods for selectively removing tar, tar-like compounds, and heavier molecules from a extraction and steam cracking recovery system by employing a membrane unit in one or more positions within the system. In particular embodiments, the system is for the extraction of 1-3 butadiene. In particular embodiments, the solvent used in the extraction process is dimethylformamide (DMF).

The membrane unit continually removes tar from the process, minimizing/eliminating the need for purging or dumping of any process stream. To accomplish this, the membrane unit may preferentially permeate extraction solvents thereof while either not permeating other molecules (e.g., tar or other heavy molecules) or permeating those other molecules more slowly in order to separate the solvent from the other molecules. In some embodiments, for example, using a polymeric membrane, the separation is not accomplished by filtering based on size of the molecules, but rather by permitting the solvent to dissolve and diffuse through the membrane unit preferentially over tar. In other embodiments, for example, using a ceramic membrane, the separation is accomplished by filtering based on size of the molecules, References will now be made in detail to example embodiments of the disclosed technology, examples of which are illustrated in the accompanying drawings and disclosed herein. Wherever convenient, the same reference numbers will be used throughout the drawings to refer to the same or like parts.

FIG. 1 illustrates the concept of membrane separation of tar from extraction solvent, including but not limited to, dimethylformamide (DMF). Feed 105 is pressurized to the membrane 110 which allows polar molecule DMF (and/or other solvent) to go through the membrane 110 under solution/diffusion mechanism to form solvent-enriched permeate 115 and tar-enriched retentate 119. Driving force for the permeating molecules, pressure differential, is provided by keeping the permeate side at lower pressure than the feed pressure.

During the extraction process, extraction solvent containing tar is circulated through a solvent loop including a tar kettle/reclaimer which acts to remove tar from the solvent loop. The reclaimer vaporizes the extraction solvent overhead where it is condensed and returned to the solvent loop. The "cleaned" solvent then returns to the extraction process for further extraction and recycling. A mixture of 70% tar and 30% solvent is left in the reclaimer, which is then pumped out for disposal.

In the process of the claimed invention, the solvent is passed through one or more membrane units upstream from the reclaimer. In certain embodiments, the solvent is passed through two or more membrane units upstream from the reclaimer. In certain other embodiments, one or more additional membrane units can be positioned downstream from the reclaimer.

Regardless of its position within the system, the membrane unit(s) may each be configured to receive and generate process streams (e.g., via one or more inlet ports and one or more outlet ports). The membrane unit(s) may each be further configured to receive a solvent/process stream at an inlet pressure of between about 50-3000 psig using a pump. In some embodiments, the inlet pressure may be constant and approximately between 200 to 2000 psig. In other embodiments, the inlet pressure may be constant and approximately between 300 to 1500 psig. In still other embodiments, the inlet pressure may be constant and approximately 130 to 800 psig. Functionally, the membrane unit(s) may each have a solvent permeance of between 1-500 $gm/m^2/hr/psi$ (e.g., between approximately 2-200 $gm/m^2/hr/psi$ in some embodiments and approximately 60 $gm/m^2/hr/psi$ or 120 $gm/m^2/hr/psi$ in other embodiments). The membrane unit(s) are designed for complete removal of tar from the permeate stream at at least 90% permeate yield. In certain embodiments, the membrane unit(s) provide for complete removal of tar from the permeate stream at at least 97% permeate yield.

In other embodiments, the membrane unit(s) provide for complete removal of tar from the permeate stream at at least 90% permeate yield. This enables the unit to operate at a 90% lower tar concentration. The circulating tar concentration thus drops from 1% to 0.1%, while remaining at the same reclaimer capacity (3 klb/hr).

In still other embodiments, the membrane unit(s) provide for complete removal of tar from the permeate stream at at least 95% permeate yield.

The inputs, outputs, and efficiency of the membrane unit(s) vary based on its position within the solvent recovery loop.

Structurally, membrane unit(s) may each include a one-stage or multi-stage (e.g., two-stage) membrane system. A one-stage system may be configured to remove approximately 90% of the tar or heavier compounds present in an inlet stream. A two-stage or other multi-stage membrane system may remove approximately 90% of the tar or heavier compounds present in an inlet stream while reducing the loss of solvent to half of that of single stage membrane system.

Adding stages to the membrane unit(s) increases purity of the solvent that it preferably permeates, though it costs more to construct and maintain.

The structure and materials of the membrane(s) making up the membrane unit(s) may vary. Similarly, like the structure and materials of the membrane(s), the position of the membrane unit(s) within the solvent recovery loop may impact its performance and overall performance of the system.

In certain embodiments, the membrane(s) may be a polymeric membrane and/or a ceramic membrane. In certain embodiments a combination of membranes are used such that both a polymeric membrane and a ceramic membrane are used in any order upstream from the reclaimer.

Figure 3:
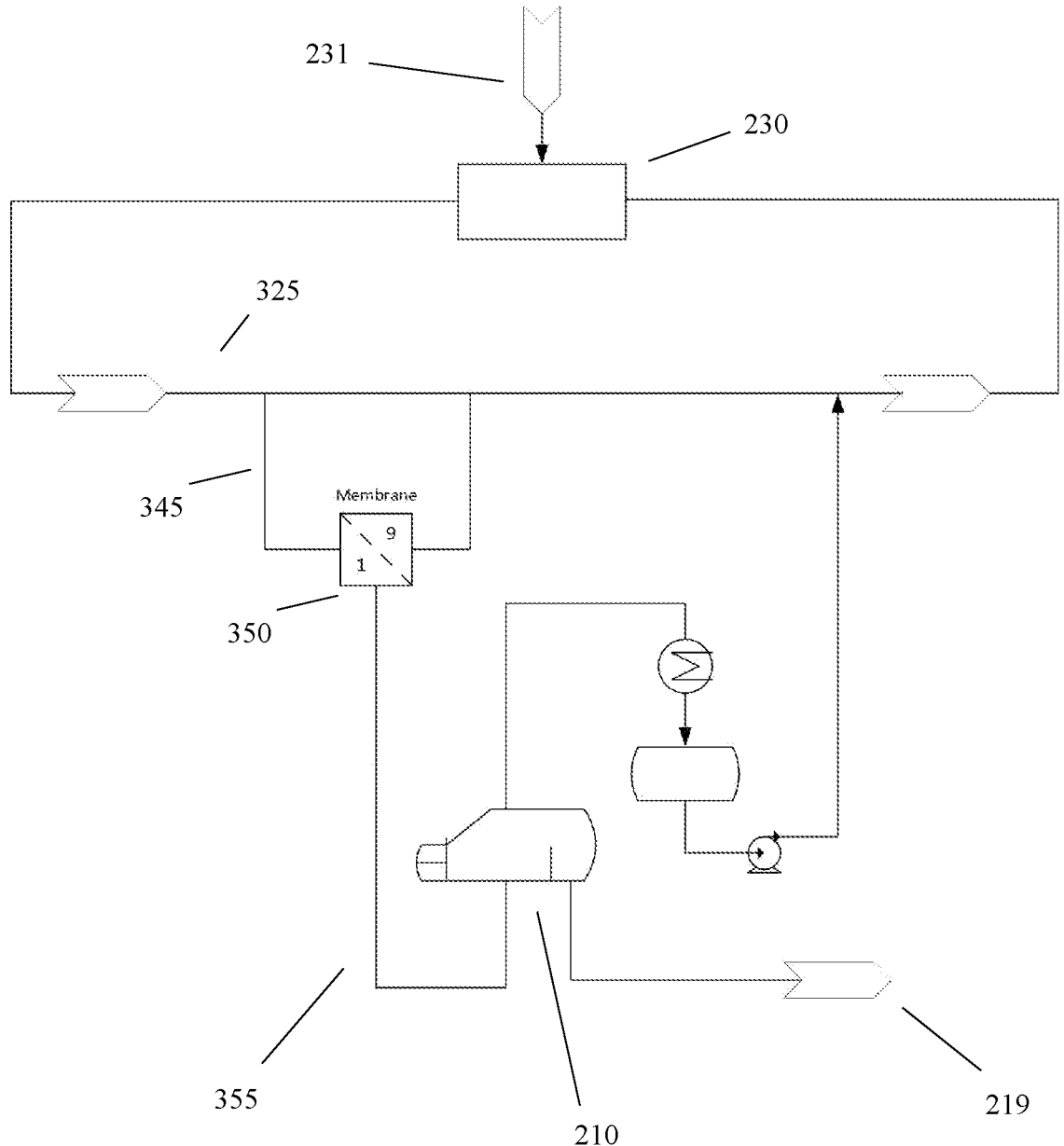
FIG. 3 is a diagram depicting an apparatus used in the membrane solvent loop/tar mass balance extraction processes of the disclosure.

Membrane Application Incentives:

Membrane implementation allows for the reduction of circulating solvent tar concentration from >1 wt % to 0.1 wt %, as illustrated in FIG. 3. This results in significant operational and efficiency savings from a reduction in equipment cleaning and related downtime.

Figure 6:
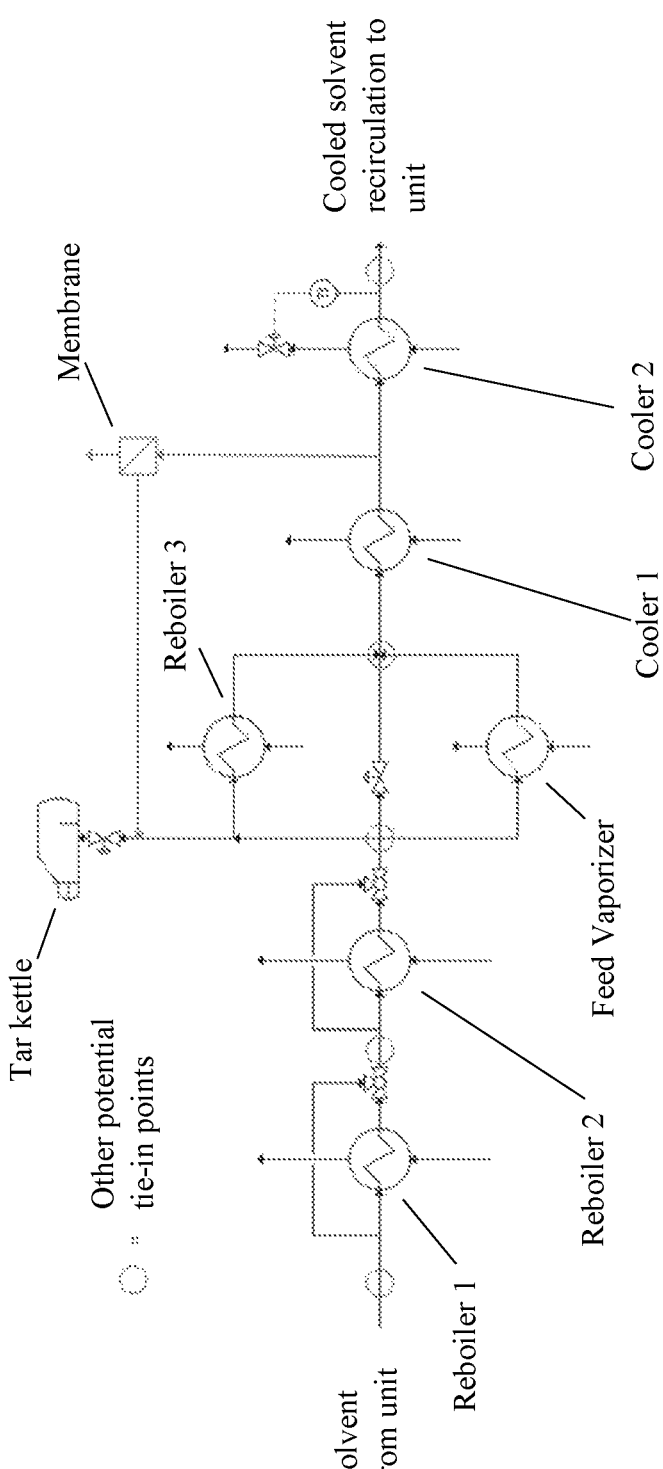
FIG. 6 is a diagram showing the heat recovery heat exchanger train on the solvent loop.

Additionally, the processes of the disclosure allow for an increase in energy savings from reduced tar fouling. FIG. 6 shows an integrated DMF solvent loop, in which hot solvent recovered from the unit is utilized for reboiling and vaporizing duty in various economizers. Any remaining heat that is not recovered in the heat exchangers is lost downstream to cooling tower water (represented as "Cooler 1" and "Cooler 2" in FIG. 6) in order to achieve a target recirculation temperature.

As the solvent loop integrated reboilers and vaporizers foul due to circulating tar, unit steam consumption increases in order to maintain heat duty. In the example application, the duty loss due to tar-based fouling is expected to be reduced by half from the lower tar concentration.

The largest impact of the membrane technology is realized by minimizing production losses due to tar-based distillation column fouling. By lowering the main fouling precursor by an order of magnitude, production losses due to distillation column fouling can be expected to reduce by at least 50% over a turnaround cycle.

While the present disclosure has been described in connection with a plurality of exemplary aspects, as illustrated in the various figures and discussed above, it is understood that other similar aspects can be used, or modifications and additions can be made, to the described aspects for performing the same function of the present disclosure without deviating therefrom. For example, in various aspects of the disclosure, methods and compositions were described according to aspects of the presently disclosed subject matter. However, other equivalent methods or compositions to these described aspects are also contemplated by the teachings herein. Therefore, the present disclosure should not be limited to any single aspect, but rather construed in breadth and scope in accordance with the appended claims.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the various patent offices and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

EXAMPLES

In order to provide a better understanding of the foregoing disclosure, the following non-limiting examples are offered. Although the examples may be directed to specific embodiments, they are not to be viewed as limiting the invention in any specific respect.

Example 1: Removal of Heavies from DMF

A feasibility test for removing heavies (tar molecules are heavier) from DMF was conducted using the feed received from Baytown chemical plant. Both inorganic/ceramic based membranes and polymeric membranes with molecular weight cut-offs between 0.15 and 1 kD were effective and rejecting the tar while allowing DMF to permeate through the membrane.

Feed was pressurized to between 50-800 psi on top of a membrane coupon. Temperature of the feed and the test cell was maintained between 30-50 C. The feed was stirred using a mechanical stirrer at 400 rpm throughout the test to prevent concentration polarization at the surface of the membrane. Permeate samples were collected at different stage cuts i.e. the fraction of feed that permeated through the membrane.

Micro-carbon residue (MCR) of the initial feed sample, permeate samples and the retentate sample were measured, where MCR can be used a relative measure of tar present in the DMF solution. The feed MCR for all tests was ~0.6 wt %. The average flux (in units of L/m2/h or LMH) was calculated over the entire stage cut range.

TABLE 2

| Run number | Membrane | T, P | Avg Flux (LMH) | Final Permeate Stage Cut | Final Permeate MCR [wt %] |
|---|---|---|---|---|---|
| 27052-086 | TAMI 1 KD Ceramic | 30 C., 80 psig | 10.2 | 90% | 0.15 |
| 27052-087 | Evonik Duramem ® 150 | 50 C., 800 psig | 1.53 | 85% | 0.10 |
| 27052-083 | Evonik Duramem ® 300 | 50 C., 600 psig | 1.82 | 10% 50% 92% | 0 0.1 0.1 |
| 27052-119 | Evonik Duramem ® 900 | 50 C., 600 psig | 1.10 | 20% 30% | 0.05 0.05 |

The Evonik Duramem series (polymeric) showed the greatest tar rejection performance, albeit at lower flux. The TAMI 1KD ceramic membrane attained much higher flux at lower applied pressure, with slightly lower tar rejection.

Example 2: Impact of Increased Tar Purge Capacity

Figure 2:
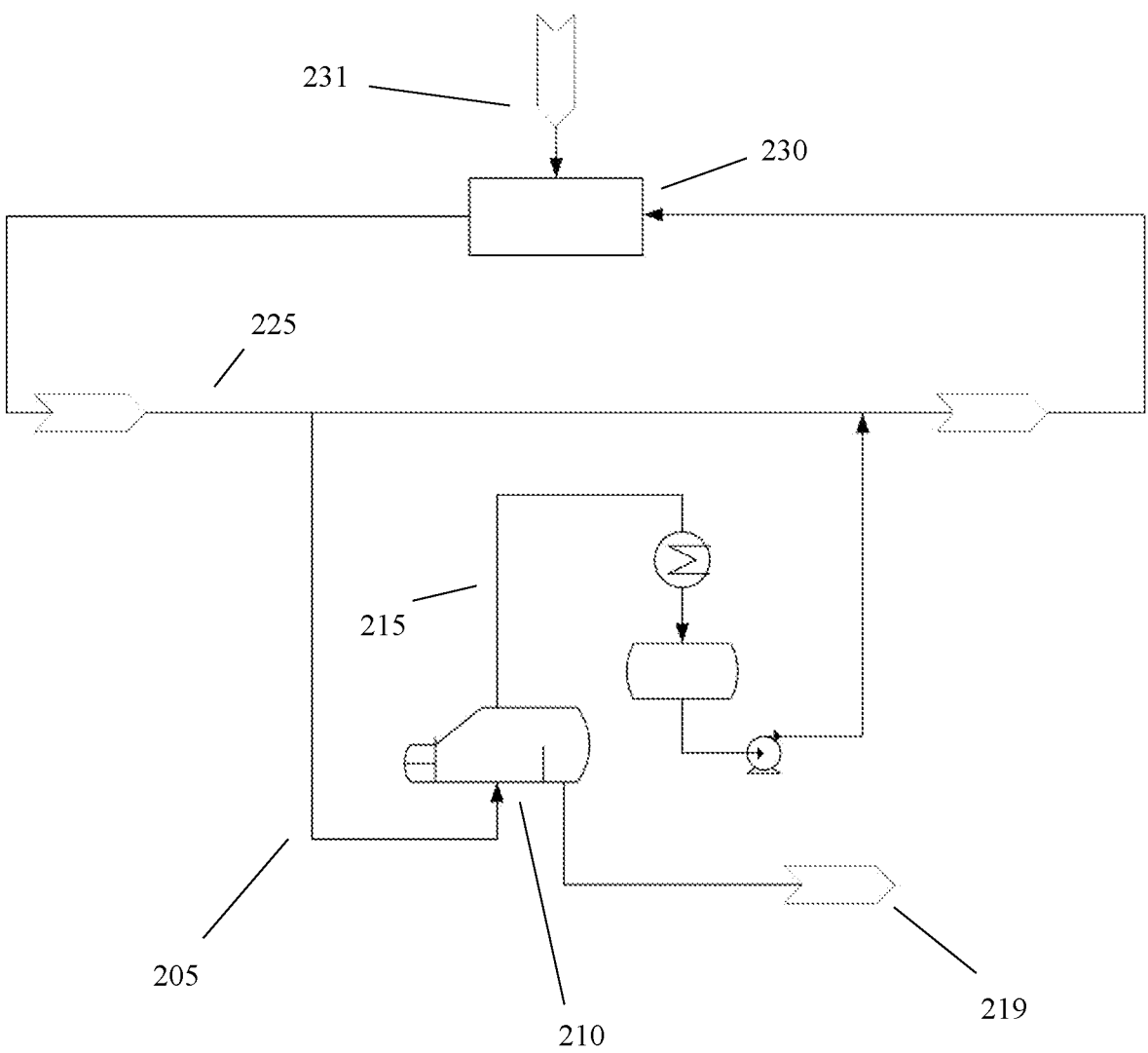
FIG. 2 is a diagram depicting an apparatus used in conventional solvent loop/tar mass balance extraction process.

FIG. 2 represents the Base Case tar removal mass balance for a model 220 kta BD extraction plant. In this example, 30 lb/hr (0.03 klb/hr) of tar is generated in the extraction process 230. Fresh solvent 231 (such as DMF) is added to maintain the volume of solvent in solvent loop 225. The tar kettle 210 receives a 3 klb/hr purge stream 205 from the solvent loop 225. Tar kettle 210 vaporizes DMF and furfural overhead, resulting in stream 215, where it is condensed and returned to the solvent loop 225. A mixture of 70% tar and 30% DMF/furfural is left in the tar kettle 210, which is then pumped out 219 for disposal.

As an example of a mass balance for the configuration shown in FIG. 2, for a 220 kta extraction plant, the flow exiting from extraction process 230 can correspond to 700 klb/hr. The composition of the flow leaving the extraction process 230 can be roughly 97 wt % DMF, 2 wt % furfural, and 1 wt % tar. This corresponds to 679 klb/hr DMF, 14 klb/hr furfural, and 7 klb/hr tar. In this example, purge stream 205 corresponds to only 3 klb/hr of the total flow, or less than 0.5% of the flow in solvent loop 225. The composition of purge stream 205 in this example is 2.91 klb/hr DMF, 0.06 klb/hr furfural, and 0.03 klb/hr tar. The remaining portion of the flow in solvent loop 225 is just recirculated. The composition of purge stream 205 is roughly the same as the flow in the solvent loop prior to the split. The purge stream 205 is then passed into tar kettle or reclaimer 210, where a portion of the tar is separated from the solvent. This results in overhead stream 215 and disposal stream 219. In this example, the composition of overhead stream 215 is 2.90 klb/hr of DMF and 0.06 klb/hr of furfural. The disposal stream 219 is then 70% tar, with roughly 0.01 klb/hr of DMF being removed as part of the disposal stream. This lost DMF is added back to the system by fresh solvent stream 231. The mass balance shown in the above example maintains the circulating tar concentration in the solvent loop at 1%.

FIG. 3 shows an adaptation of the Base Case, where a membrane 350 capable of processing 10× the historical maximum tar purge rate has been installed upstream of the tar kettle or reclaimer 210. The membrane 350, designed for complete removal of tar from the permeate stream at 90% permeate yield, enables the unit to operate at a 90% lower tar concentration. Thus, relative to the mass balance example described above, purge stream 345 in the configuration shown in FIG. 3 can have a flow of 30 klg/hr, rather than the 3 klb/hr for purge stream 205 in the configuration shown in FIG. 2. Additionally, because more tar can be removed per pass, for the mass balance example described above, adding membrane 350 can reduce the circulating tar concentration in solvent loop 325 from 1% to 0.1%, while remaining at the same capacity (3 klb/hr) for tar kettle or reclaimer 210. Thus, in an example mass balance for the configuration shown in FIG. 3, the composition of a 700 klb/hr flow can be 685.3 klb/hr of DMF, 14 klb/hr of furfural, and 0.7 klb/hr of tar. The composition of retentate stream 355 exiting from membrane 350 can be 2.91 klb/hr DMF, 0.06 klb/hr furfural, and 0.03 klb/hr tar. In other words, the retentate stream 355 in FIG. 3 has a similar composition to purge stream 205 in FIG. 2. Tar concentration reduction is the basis for the unit-wide benefit of fouling minimization and reduced unit downtime for maintenance.

Figure 4:
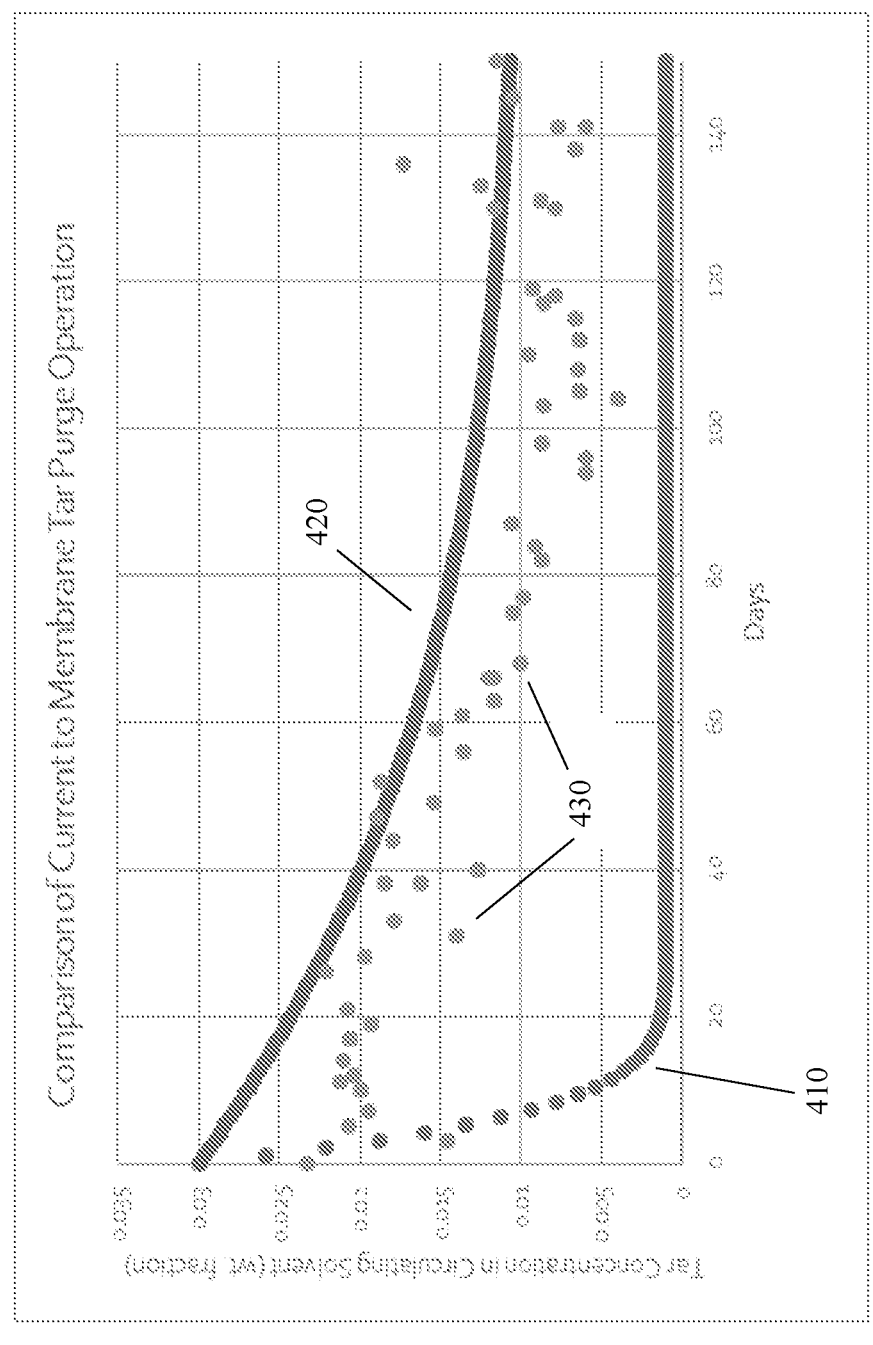
FIG. 4 is a plot showing the result of modelling the unit tar removal process as a continuous stirred-tank reactor of the conventional solvent loop/tar mass balance extraction process as compared to the membrane solvent loop/tar mass balance extraction processes of the disclosure.

The impact of the increased tar purge capacity from the membrane is demonstrated in FIG. 4 by modelling the dynamic response of each system (the 3 klb/hr vs the 30 klb/hr) purge to an upset scenario with a starting tar concentration of 3 wt %. In FIG. 4, line 410 is data from a modeling a membrane system with a configuration roughly corresponding to FIG. 3. Line 420 is data from modeling a configuration roughly corresponding to the base case configuration in FIG. 2. Line 430 corresponds to data from testing in a butadiene unit as described in more detail below.

The membrane allows for tar concentration of the circulating solvent to decrease quicker due to the tar removal rate beginning at an order of magnitude higher than the existing system. For the membrane system in line 410, ultimately, the membrane system reaches equilibrium at 0.1 wt %. Alternatively, the existing tar purge system represented by model line 420 can only return to the baseline 1 wt % due to its constrained tar removal rate through the kettles.

The system response shown in lines 410 and 420 of FIG. 4 is the result of modelling the unit tar removal process as a continuous stirred-tank reactor. Each system starts with the same initial tar concentration, the same rate of tar generation from the extractive process, and the same system volume. The one difference, however, is the elevated purge rate enabled by the membrane system. This additional purge capacity decreases both the residence time of tar in the modelled system (greater purge rate with respect to total system volume) as well as the final equilibrium concentration (greater purge rate with respect to tar generation rate).

Validation of the derived model represented in FIG. 4 is provided by data points 430, taken from an actual plant test in a butadiene extraction unit. The unit, using a tar purge system consistent with FIG. 3 responded to tar concentrations approaching 3 wt % by raising the purge rate to the maximum 3 klb/h. As seen in data points 430 in FIG. 4, the system reached an equilibrium at ~1 wt % tar in the solvent.

Example 3: Dynamic Example of Membrane System

Figure 5:
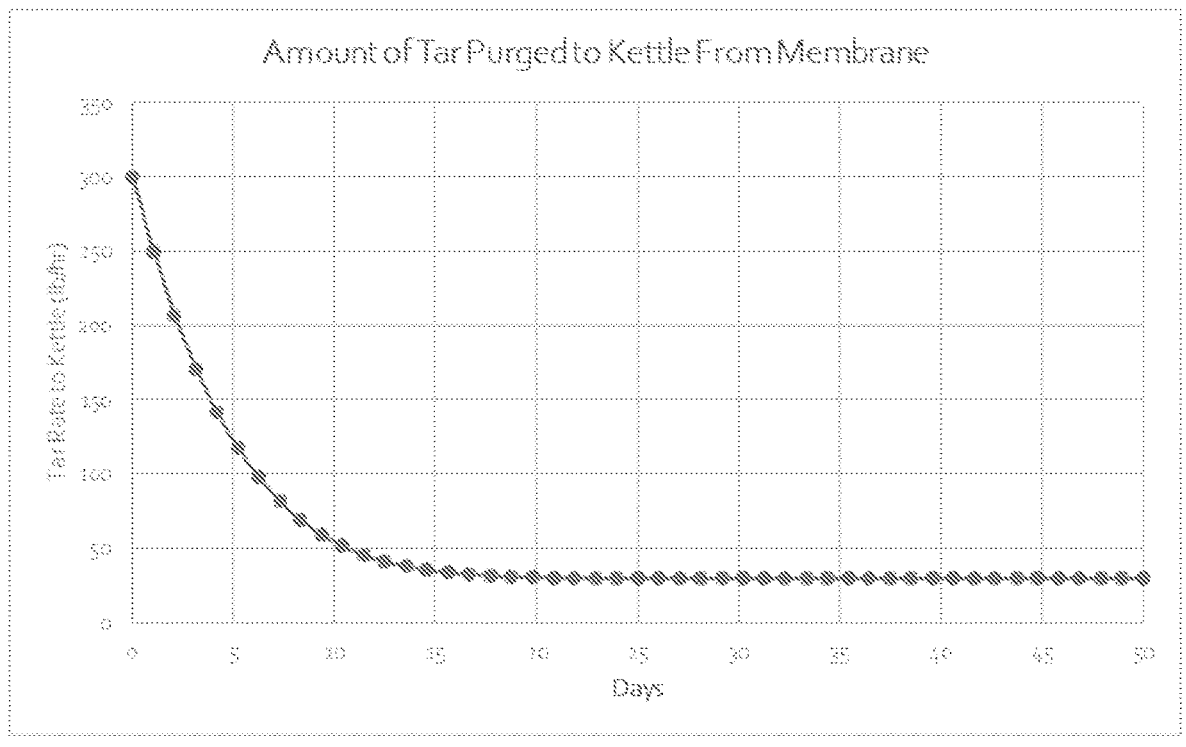
FIG. 5 is a plot showing the actual rate of tar purged to the reclaimer after implementation of the membrane operating at 30 klb/h of feed.

The data shown in FIG. 5 represents the transient period between the mass balances shown in FIGS. 2 and 3. When 30 klb/h of solvent operating with 1 wt % tar is first introduced to the membrane, it can be expected that all 300 lb/hr of tar will exit the membrane and feed the tar kettle. Consequently, the process can expect for the tar kettle to require about 10% of the normal time to fill. As the total amount of tar circulating in the system decreases, the total tar purged to the kettle (and subsequently from the unit) will equilibrate at 30 lb/hr.

Example 4: Membrane System Sizing

The membrane flux through the membrane was found to be function of tar concentration on the feed side. Flux remained relatively steady through the membrane at 2.75 g/hr up to 60% of the feed permeating through the membrane. After that, flux continued to gradually drop as more feed permeated through the membrane. The average flux through the membrane from 60% permeate to 90% permeate was measured to be close to 2.25 gm/hr.

Membrane area used in the lab experiments was 14.6 cm2.

The permeate flux, therefore, was 1.884 kg/m$^2$/hr up to 60% of the feed permeating through the membrane. This flux dropped to average flux of 1.541 kg/m$^2$/hr when 60 to 90% of the feed was permeating through the membrane.

Feed rate to the membrane in the simulation above is 30 klb/hr and the permeate is 27 klb/hr, ie., 90% of the feed is permeating.

Membrane area required for permeating 60% of 30 klb/hr feed (18 klb/hr) is (18000/2.204)/1.884=4720 m$^2$ membrane area Membrane area required for permeating from 60 to 90% of 30 klb/hr (9 klb/hr) is (9000/2.204)/1.541=2650 m$^2$ membrane area Total membrane area for the membrane system would be 7370 m$^2$

ADDITIONAL CLAUSES OF THE INVENTION

Clause 1. A method for removing tar from the solvent stream of an extraction unit, comprising:

feeding a solvent stream containing tar into a solvent recycle loop comprising a membrane unit;

preferentially permeating solvent in the solvent stream via the membrane unit to separate a tar rich stream from a membrane unit product stream; and feeding the membrane unit product stream into the solvent recycle loop for recirculation within the solvent recycle loop.

Clause 2. The method of Clause 1, wherein the solvent recycle loop further comprises a reclaimer.

Clause 3. The method of any one of Clauses 1-2, further comprising a step of processing the tar rich stream in the reclaimer, wherein the processing deposits tar into a tar kettle for removal from the extraction unit and produces a reclaimer treated stream.

Clause 4. The method of Clause 3, wherein the reclaimer treated stream is fed into the solvent recycle loop for recirculation within the solvent recycle loop.

Clause 5. The method of any one of Clauses 1-4, wherein the solvent stock stream comprises dimethylformamide.

Clause 6. The method of any one of Clauses 1-5, wherein preferentially permeating the solvent from the solvent stream via the membrane unit further comprises feeding the solvent stream into the membrane unit at a constant pressure between 50 to 3000 psig.

Clause 7. The method of any one of Clauses 1-6, wherein the membrane unit comprises a one-stage membrane system.

Clause 8. The method of any one of Clauses 1-7, wherein the membrane unit comprises a multi-stage membrane system.

Clause 9. The method of any one of Clauses 1-8, wherein the membrane unit presents a solvent permeance of 120 gm/m$^2$/hr/psi.

Clause 10. The method of any one of Clauses 1-9, wherein the membrane unit is positioned upstream from the reclaimer.

Clause 11. The method of any one of Clauses 1-10, wherein the solvent recycle loop comprises one or more additional membrane units.

Clause 12. The method of any one of Clauses 2-11, wherein one or more additional membrane units are positioned between the membrane unit and the reclaimer.

Clause 13. The method of Clause 12, wherein the one or more additional membrane units are positioned downstream from the reclaimer.

Clause 14. A 1-3 butadiene extraction system, comprising:

an extraction unit configured to extract 1-3 butadiene from a solvent;

a solvent recycling loop configured to remove solvent containing tar or other heavy impurities from the extraction unit and to return cleaned solvent into the extraction unit;

one or more membrane units configured to receive solvent containing tar or other heavy impurities and to separate membrane-cleaned solvent from tar-rich solvent;

a reclaimer configured to receive tar-rich solvent and to extract tar or other heavy impurities from reclaimer-cleaned solvent; and one or more recycling inlet ports configured to return the membrane-cleaned solvent and the reclaimer-cleaned solvent to the solvent recycling loop.

Clause 15. The system of Clause 14, wherein the solvent containing tar or other heavy impurities is fed into the membrane unit at a constant pressure between 50 to 3000 psig.

Clause 16. The system of any one of Clauses 14-15, wherein the membrane unit comprises a one-stage membrane system.

Clause 17. The system of any one of Clauses 14-16, wherein the membrane unit comprises a multi-stage membrane system.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired products, additional ingredients may be added, and/or similar ingredients may be substituted for one or more of the ingredients described.

Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A method for removing tar from the solvent stream of an extraction unit, comprising:

feeding a solvent stream containing tar into a solvent recycle loop comprising a membrane unit;

preferentially permeating solvent in the solvent stream via the membrane unit to separate a retentate stream comprising solvent and a greater wt % of tar than a wt % of tar in the solvent stream from a permeate stream comprising tar and a greater wt % of solvent than a wt % of solvent in the solvent stream;

feeding the permeate stream into the solvent recycle loop for recirculation within the solvent recycle loop, and processing the retentate stream in a tar kettle, the processing comprising depositing tar into the tar kettle for removal from the extraction unit, the processing producing a tar kettle-treated stream.

2. The method of claim 1, wherein the tar kettle-treated stream is fed into the solvent recycle loop for recirculation within the solvent recycle loop.

3. The method of claim 1, wherein the solvent stream comprises dimethylformamide.

4. The method of claim 1, wherein preferentially permeating the solvent from the solvent stream via the membrane unit further comprises feeding the solvent stream into the membrane unit at a constant pressure between 50 to 3000 psig.

5. The method of claim 1, wherein the membrane unit comprises a one-stage membrane system.

6. The method of claim 1, wherein the membrane unit comprises a multi-stage membrane system.

7. The method of claim 1, wherein the membrane unit presents a solvent permeance of 120 $gm/m^2/hr/psi$.

8. The method of claim 1, wherein the membrane unit is positioned upstream from the tar kettle.

9. The method of claim 1, wherein the solvent recycle loop comprises one or more additional membrane units.

10. The method of claim 9, wherein one or more additional membrane units are positioned between the membrane unit and the tar kettle.

11. The method of claim 10, wherein the one or more additional membrane units are positioned downstream from the tar kettle.

12. A method for removing tar from the solvent stream of an extraction unit, comprising:

feeding a solvent stream containing tar and dimethylformamide into a solvent recycle loop comprising a membrane unit;

preferentially permeating dimethylformamide in the solvent stream via the membrane unit to separate a retentate stream comprising a greater wt % of tar than a wt % of tar in the solvent stream from a permeate stream comprising a greater wt % of dimethylformamide than a wt % of dimethylformamide in the solvent stream; and feeding the permeate stream into the solvent recycle loop for recirculation within the solvent recycle loop.

13. The method of claim 12, wherein the solvent recycle loop further comprises a tar kettle.

14. The method of claim 13, further comprising a step of processing the retentate stream in the tar kettle, wherein the processing deposits tar into the tar kettle for removal from the extraction unit and produces a tar kettle-treated stream.

15. The method of claim 12, wherein preferentially permeating the solvent from the solvent stream via the membrane unit further comprises feeding the solvent stream into the membrane unit at a constant pressure between 50 to 3000 psig.

16. The method of claim 12, wherein the membrane unit presents a solvent permeance of 120 $gm/m^2/hr/psi$.

17. The method of claim 12, wherein the membrane unit is positioned upstream from the tar kettle.

* * * * *